US 6,716,635 B2

(12) United States Patent
Jacobson et al.

(10) Patent No.: US 6,716,635 B2
(45) Date of Patent: Apr. 6, 2004

(54) METHOD FOR IDENTIFYING REGULATORS OF PROTEIN-ADVANCED GLYCATION END PRODUCT (PROTEIN-AGE) FORMATION

(75) Inventors: Elaine L. Jacobson, Tucson, AZ (US); Myron K. Jacobson, Tucson, AZ (US); Georg T. Wondrak, Tucson, AZ (US)

(73) Assignee: University of Kentucky Research Foundation, Lexington, KY (US)

( * ) Notice: Subject to any disclaimer, the term of this patent is extended or adjusted under 35 U.S.C. 154(b) by 234 days.

(21) Appl. No.: 09/836,576

(22) Filed: Apr. 16, 2001

(65) Prior Publication Data

US 2002/0037496 A1 Mar. 28, 2002

Related U.S. Application Data

(60) Provisional application No. 60/197,829, filed on Apr. 14, 2000.

(51) Int. Cl.[7] .............................................. G01N 33/00
(52) U.S. Cl. ....................................................... 436/87
(58) Field of Search ............................................ 436/87

(56) References Cited

U.S. PATENT DOCUMENTS 6,046,340 A    4/2000   Seguin et al.

FOREIGN PATENT DOCUMENTS

FR       2 776 188        11/1995

OTHER PUBLICATIONS

Cervantes–Lauren, et al., "Glycation and Glycoxidation of Histones by ADP–Ribose"; J.Biol.Chem. 271(18):10461–10469 (1996).

*Primary Examiner*—Sandra E. Saucier
(74) *Attorney, Agent, or Firm*—Fulbright & Jaworski

(57) ABSTRACT

The invention relates to methods for identifying compounds which affect cellular stress. In particular, the method relates to identifying compounds which inhibit protein advanced glycation end product formation, where the compounds are carbonyl scavengers which inhibit the formation. The assay involves combing the substance of interest with histone H1 and ADP-ribose, and then measuring fluorescence and protein cross linking. Various inhibitors of protein AGE glycation have been identified, using this assay.

7 Claims, 19 Drawing Sheets

Confirming Potential Positives II: Protein Electrophoresis

ADPR omitted    Control    AG

R = CH₃ or C₆H₅

■ : no methylglyoxal
▲ : methylglyoxal (300 μM)
● : methylglyoxal (600 μM)
D-P : D-penicillamine

METHOD FOR IDENTIFYING REGULATORS OF PROTEIN-ADVANCED GLYCATION END PRODUCT (PROTEIN-AGE) FORMATION

RELATED APPLICATIONS

This application claims priority of provisional application No. 60/197,829, filed on Apr. 14, 2000, incorporated by reference.

STATEMENT RE GOVERNMENT GRANTS

The research underlying this invention was supported, in part, by NIH grants CA43894 and NS538496.

FIELD OF THE INVENTION

This invention relates to a method for identifying inhibitors of protein-advanced glycation end product ("Protein-AGE" hereafter) formation. The methodology is useful in determining substances of interest in impacting pathological conditions with which protein-AGE formation is associated, such as diabetes, atherosclerosis, chronic neurodegenerative diseases, such as Alzheimer's disease, skin photoaging, and other degenerative diseases characteristic of the aging process.

BACKGROUND AND PRIOR ACT

Glycation, as used herein, is a non-enzymatic, posttranslational modification of proteins by reducing sugars and other reactive carbonyl species, which adversely affect protein function. Tissue deterioration and aging have been widely associated with accumulation of damage from chemical processes induced by glycation, as well as oxidative stress and UV irradiation. The accumulation in long lived proteins of glycation products and AGE products derived from glycation has been implicated in a number of age-related diseases including long term diabetic complications (Thorpe, et al., Drugs Aging 9: 69–77 (1996)), atherosclerosis (Ruderman, et al., FASEB J. 6:2905–2914 (1993); erratum FASEB J. 7(1):237 (1993)), Alzheimer's disease (Vitek, et al., Proc. Natl. Acad. Sci. USA 91:4766–4770 (1994)), skin photo aging (Mizutani, et al., J.Invest. Dermatol 797–802 (1997) and in the general pathology of the aging process (Frye, et al., J. Biol Chem 273:18714–18719 (1998)). Long term diabetic complications from hyperglycemia eventually cause serious and life threatening pathologies such as end-stage renal disease (Baynes, et al., Diabetes 40:405–412 (1991)). Irreversible microvascular and macrovascular complications including retinopathy, neuropathy, nephropathy, atherosclerosis, and cerebrovascular disease all have been linked mechanistically to the formation of protein-AGE in connective tissue, especially on collagen, and matrix protein components. Moreover, similar events occurring at a slower rate seem to be of equal relevance for the normal aging process. (Thorpe, et al., supra).

Glycation and subsequent protein-AGE formation plays a central role in cellular carbonyl stress and glucose toxicity. Administering the glycation inhibitor aminoguanidine effectively suppresses secondary complications in rodents with experimental diabetes (Edelstein, et al., Diabetologica 35:96–97 (1992)); however, aminoguanidine is a hydrazine derivative that shows systemic toxicity upon long-term administration, since it is a potent inhibitor of catalase (Ou, et al., Biochem Phamacol 46:1139–1144 (1993)) and inducible nitric oxide synthase (Okuda, et al., J. Neuroimmunol 81:201–210 (1998)). The toxicity profile of aminoguanidine makes it unlikely that it will be used clinically. Therefore, an urgent clinical need exists for the identification and characterization of new compounds that effectively inhibit glycation and its associated pathological consequences. A high throughput screening assay that could be applied to large combinatorial compound libraries would likely lead to the identification of new glycation inhibitors.

Reactive oxygen species ("ROS"), and reactive carbonyl species ("RCS"), especially dicarbonyl compounds, are key mediators of cellular damage caused by oxidative stress, glycation and UV radiation. The origin of cellular carbonyl stress as a result of glycation, lipid peroxidation, sugar autooxidation and metabolism can be seen in, e.g., FIG. 1. Oxygen dependent and independent pathways lead to the formation of various reactive carbonyl species, including 2-dicarbonyls like methylglyoxal and glyoxal, as key intermediates for the accumulation of protein damage by AGE formation. Carbonyl stress additionally originates from the metabolic generation of methylglyoxal. Briefly, early glycation products are derived from the reaction of a reducing sugar with protein amino groups (lysine and arginine) to generate aldimines (Schiff base adducts) that can undergo the Amadori rearrangement to form ketoamine adducts (Hodge, et al., J. Am. Chem Soc. 75:316–322 (1953)). Protein-AGE are generated from early glycation products by both oxidative and non-oxidative pathways in which a variety of reactive dicarbonyl compounds such as glyoxal, methylglyoxal, and 3-deoxyosones are suggested intermediates (Thornalley, et al., Biochem J. 344:109–116 (1999)).

Protein-AGE include protein N-(carboxymethyl)lysine residues (CML) (Ahmed, et al., J. Biol. Chem 261:4889–4894 (1986)), and a heterogeneous group of complex modifications such as pentosidine (Sell, et al., J. Biol. Chem. 264:21597–21602 (1989)) that are characterized by their high fluorescence and ability to cause protein-protein cross-links. Accumulation of AGE-specific fluorescence (ex. 370 nm; em. 440 nm) is a general measure of overall protein damage and it is a widely used tool of glycation research in vitro and in vivo. In some cases, reactive dicarbonyl compounds may form by auto-oxidation of the sugar itself without requiring glycation, and the presence of trace amounts of transition metal ions (Fe, Cu) has been implicated in the formation of dicarbonyl compounds and reactive oxygen species such as hydrogen peroxide (Elgawish, et al., J. Biol. Chem 271:12964–12971 (1996)). Amino acids other than lysine and arginine are also modified by glycoxidation. For example, surface exposed methionine residues in proteins are very sensitive to protein oxidation (Hall, et al., Biochem. Biophys. Acta 1121:325–330 (1992)).

Due to its abundance, glucose is assumed to be a major source of glycation and protein-AGE formation in extracellular proteins in vivo; however, glucose is only a weak glycation agent and the chemical reaction with proteins under physiological conditions occurs only over months and years (Higgins, et al., J. Biol. Chem 256:5204–5208 (1981)). In contrast to glucose, the more reactive pentoses have been implicated as sugar sources for the glycoxidation of intracellular proteins, because they are much more efficient precursors for the formation of fluorescent AGE such as pentosidine (Sell, et al., supra). An abundant cellular pentose is ADP-ribose, which is generated from NAD by multiple metabolic pathways (Cervantes-Laurean, et al., Biochemistry 32:1528–1534 (1993); Jacobson, et al., Mol. Cell Biochem. 138:207–212 (1994)). Earlier studies have focused on a pathway that involves the intranuclear generation of ADP-ribose (ADPR). Research has demonstrated that the cell nucleus is a likely site for glycation in vivo by ADP-ribose.

Oxidative stress and other conditions that cause DNA strand breaks stimulate the synthesis of nuclear polymers of ADP-ribose, which are rapidly turned over generating ADP-ribose in close proximity to the long lived histones rich in lysine and arginine residues (Cervantes-Laurean, et al., supra.

In addition to the above referenced items, tissue deterioration and aging have been widely associated with accumulation of damage from chemical processes induced by oxidative stress, glycation, and UV-irradiation. Halliwell, et al., Free Radicals in Biology and Medicine (Clarendon Press, Oxford, 1989). Berlett, et al., J. Biol Chem 272:20313–20316 (1997). All of these are potent inducers of Reactive Oxygen Species ("ROS") and Reactive Carbonyl Species ("RCS").(Anderson et al., J. Chem, Invest. 104:103–113 (1999)), which are key intermediates of accumulative protein damage during general aging and several pathological conditions, e.g. chronic inflammatory diseases (Dimon-Gadal, et al., J. Invest. Dermatol 114:984–989 (2000)); psoriasis, and diabetes. Brownlee, et al., Ann. Rev. Med 46:223–234 (1995); Brinkmann, et al., J. Biol Chem 273:18714–18719 (1998)). RCS as reactive intermediates of cellular carbonyl stress originate from a multitude of mechanistically related pathways, like glycation (Thornalley, et al., BioChemJ 344:109–116 (1999), sugar autoxidation (Wolffi, et al., Prog. Clin. Biol. Res 304:259–75 (1989), lipid peroxidation (Fu, et al., J. Biol Chem 271:9982–64996), and UV-photodamage (Mizutani, et al., J. Invest. Dermatol 108:797–802 (1997)). Glycation, a spontaneous aminocarbonyl reaction between reducing sugars and long-lived proteins is a major source of RCS production leading to cellular carbonyl stress. Reactive $\alpha$-dicarbonyl intermediates, such as glyoxal, methylglyoxal, and 3-deoxyosones, are generated by both oxidative (glycoxidative) and non-oxidative reaction pathways of glycation. The complex reaction sequence is initiated by the reversible formation of a Schiff base, which undergoes an Amadori rearrangement to form a relatively stable ketoamine product during early glycation. A series of further reactions involving sugar fragmentation and formation of $\alpha$-dicarbonyl compounds as key reactive intermediates yields stable protein-bound advanced glycation end products (AGEs) (Thornalley, et al., supra; Glomb, et al., J. Biol. Chem 270:10017–10026 (1995); Wondrak, et al., Free Radical Biol. Med. 29:557–567 (2000)). Lander, et al., J. Biol Chem 272: 17810–14 (1997). Interestingly, RCS and AGEs can exert their detrimental cellular effects by increasing ROS production, thereby forming a vicious cycle of ROS and RCS production. AGE-formation is accompanied by accumulation of AGE-specific fluorescence ($\lambda$ex-370 nm, $\lambda$em-440 nm) and protein crosslinking, which are measures of overall protein damage in tissue. Brownlee, et al., supra. The arginine-derived imidazolium AGE-products (Westwood, et al., J. Protein Chem 14:359–72 (1995); the glyoxal-lysine dimer (GOLD) and the methylglyoxal-lysine dimer (MOLD) (Brinkmann, et al., J. Biol Chem 273:18714–18719 (1998)) have been identified in aged human lens crystallin and skin collagen implicating $\alpha$-dicarbonyl stress in tissue aging. Additionally, RCS like glyoxal, the direct precursor of the AGE $N^E$-carboxymethyl-L-lysine (CML), are generated by free radical damage to polyunsaturated fatty acids in cellular membranes. Fu, et al., supra. UV-irradiation is another source of tissue carbonyl stress, as evidenced by the accumulation of CML in sun exposed lesions of actinic elastosis. Mizutani, et al., supra. Therefore, AGE-products like CML and GOLD may be regarded as biomarkers of tissue carbonyl stress.

Methylglyoxal is an important glycation intermediate (Thornalley, et al., supra) that is also generated as a biological metabolite by nonenzymatic and enzymatic degradation of glycolytic triose phosphate intermediates and from threonine catabolism. (Thornalley, et al., Gen. Pharmac 27:565–573 (1996)). Increased levels of methylglyoxal are found in blood from diabetic patients (Beisswenger, et al., Diabetes 48:198–202 (1999)), and in the lens of streptozotocin-induced diabetic rats. A recent study on the formation of AGEs in endothelial cells cultured under hyperglycemic conditions indicated that methylglyoxal was the major precursor of AGEs (Shinohara, et al., J. Clin. Invest. 101:1142–7 (1998)). Various methylglyoxal-derived AGEs have been identified in human tissues, such as fluorescent 5-methylimidazolone-derivatives, in atherosclerotic lesions of aorta (Uchida, et al., FEBS Lett 410:313–318 (1997)), or MOLD and $N^E$-carboxyethyl-L-lysine in aged skin collagen (Brinkmann, et al., supra). Recently, the cytotoxic effects of the glycation intermediates methylglyoxal and 3-deoxyglucosone on neuronal cells such as PC12 cells (Suzuki, et al., J. Biochem (Tokyo) 123:353–7 (1998)) and cultured cortical neurons (Kikuchi, et al., J. Neurosci Res 57:280–289 (1999)) have attracted considerable attention because of their suspected participation in the pathogenesis of neurodegenerative diseases such as Alzheimer's disease (Vitek, et al., Proc. Natl. Acad Sci USA 91:4766–70 (1994)) and amyotrophic lateral sclerosis (Shinpo, et al., Brain Res. 861:151–9 (2000)).

As another result of oxidative and carbonyl stress, protein damage by carbonylation has been associated with aging and a number of diseases, such as the premature aging diseases, Progeria, and Werner's syndrome (Berlett, et al., J. Biol Chem 272:20313–20316(1997)). The amount of carbonyl groups in human skin fibroblast proteins strongly correlates with the age of the donor (Oliver, et al., J. Biol Chem 262:5488–5491 (1987). Recently, elevated levels of histone H1 carbonylation in vivo as an indicator of nuclear oxidative and glycoxidative stress have been reported. (Wondrak, et al Biochem. J. 351:769–777 (2000)).

In contrast with their therapeutic potential, only a very limited number of biological inhibitors of cellular carbonyl stress, like the nucleophilic carbonyl scavenger glutathione, have been identified to date. However, some inhibitors of glycation interfere with the reaction by trapping intermediate $\alpha$-dicarbonyls, whereas other inhibitory substances act merely as antioxidants and transition metal chelators, thereby inhibiting advanced glycoxidation, but not glycation (Elgwash, et al., J. Biochem. 271:12964–71 (1996)). Systemic administration of the hydrazine derivative and carbonyl reagent aminoguanidine, a member of the first class of glycation inhibitors, effectively suppresses secondary complications in diabetic rodents with experimental diabetes and inhibits skin collagen crosslinking (Edelstein, et al., Diabetes 41:26–9 (1992); Fu, et al., Diabetes 43: 676–683 (1994)). Recently, a nucleophilic bidentate, phenylacylthiazolium bromide, has been shown to protect E. coli against methylglyoxal toxicity (Ferguson, et al., Chem. Res. Tox 12:617–622 (1999)). Other nucleophilic compounds acting as carbonyl traps like tenilsetam (Shoda, et al., Endocrinol 138:1886–92 (1997)), pyridoxamine (Onorato, et al., J. Biol. Chem 275:21177–21184 (2000)) and metformin (Ruggiero-Lopez, et al., Biochem) are being evaluated for prevention of secondary diabetic complications.

In vitro-screening for potential $\alpha$-dicarbonyl scavengers is complicated by the nature of most of the currently employed glycoxidative reaction systems, which measure the suppression of oxygen dependent AGE-formation as assessed by AGE-fluorescence or immunological quantification of specific AGEs like CML (Elgawish, et al., supra;

Shoda, et al., supra, Ruggiero-Lopez, et al., supra). Consequently, in these glycoxidation systems AGE-formation is effectively inhibited by compounds with antioxidant and metal chelating activity. Recently, oxygen-independent advanced glycation by pentoses with formation of AGE-fluorescence and protein crosslinking has been demonstrated and mechanistically linked to nonoxidative formation of deoxypentosones as reactive α-dicarbonyl intermediates (Litchfield, et al., Int. J. Biochem Cell Biol 31:1297–1305 (1999)).

The foregoing shows that there is an urgent need for the identification and characterization of compounds which effectively inhibit glycation and its associated pathological consequences. Such an assay would be useful in, e.g., analyzing large combinatorial libraries, so as to identify relevant compounds. Such an assay was described in the provisional application referred to supra, and is also described herein. Also see Wondrak, et al., Biochem J. 351:769–777 (2000) incoporated by reference. The work described therein has been pursued further, so as to develop a high throughout screening assay for identifying glycation inhibitors which act as carbonyl scavengers. Prior to these developments, several assay methods had been developed to identify glycation inhibitors for research purposes (Khalifah, et al., Biochem Biophys Res Commun 257:251–258 (1999); Rahbar, et al., Clin. Chem. Acta 287:123–130 (1999); Ruggiero-Lopez, et al., Biochem. Pharmacol 58:1765–1773 (1999)). Parameters that are measured are usually AGE-specific fluorescence, protein cross-linking, and immunological determination of protein-AGE. Most glycation assays employ glucose or a pentose as glycation agent resulting in a slow reaction requiring several weeks for development. These assays typically use non-physiological sugar concentrations or phosphate buffers to increase the rate of the reactions. The sensitivity as measured by level of detection of AGE-formation is low and the precision of the assays is also limited by low signal to noise ratios. The most sensitive assays rely on immunological assessment of AGE-formation by ELISA. Antibodies to AGE used in these assays are either extremely expensive or not commercially available. Hence, it is extremely desirable to have available inexpensive, rapid, easy-to-implement assay for identifying inhibitors of protein glycation, such as inhibitors of non-oxidative protein glycation. It is also desirable to have assays available which mechanistically, do not identify antioxidants, but materials like carbonyl scavengers. Such assays had been developed by the inventors, as will be seen in the description which follows.

DETAILED DESCRIPTION OF PREFERRED EMBODIMENTS

Figure 1:
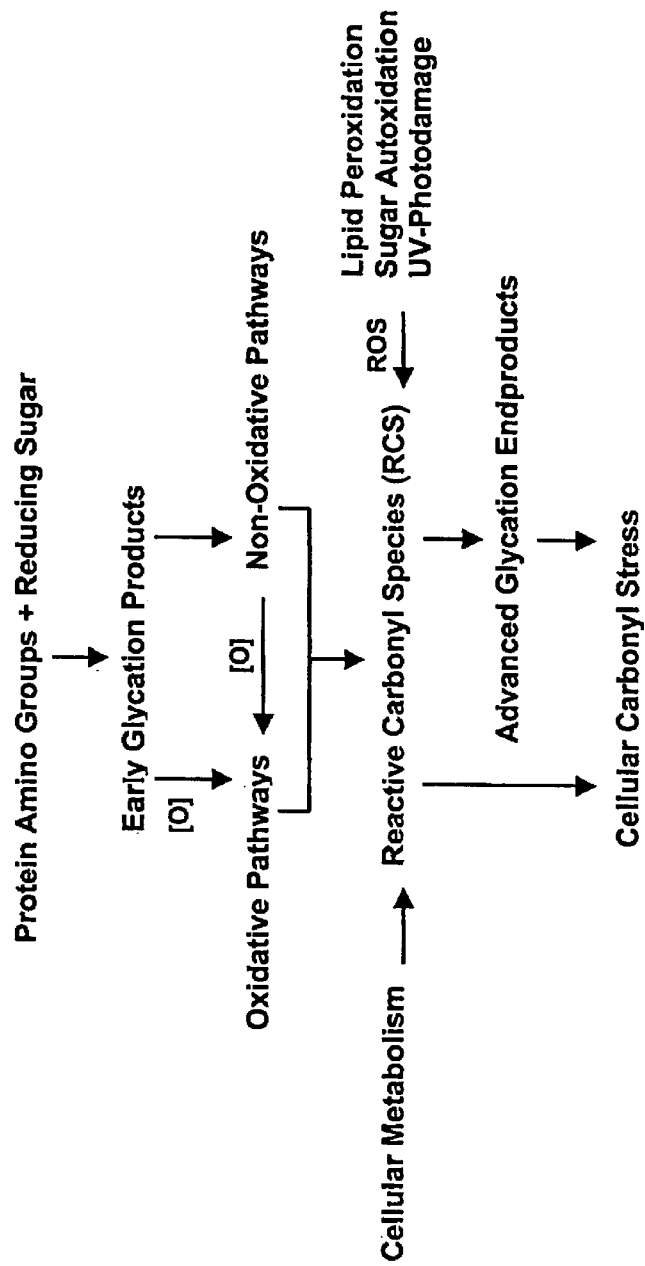
FIG. 1 provides an overview of protein glycation.
Figure 2:
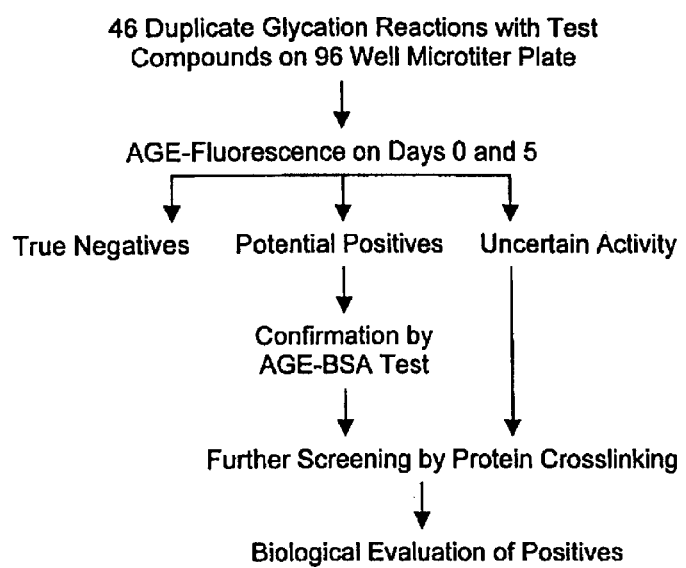
FIG. 2 shows the pathway by which ADPR is generated.
Figure 3:
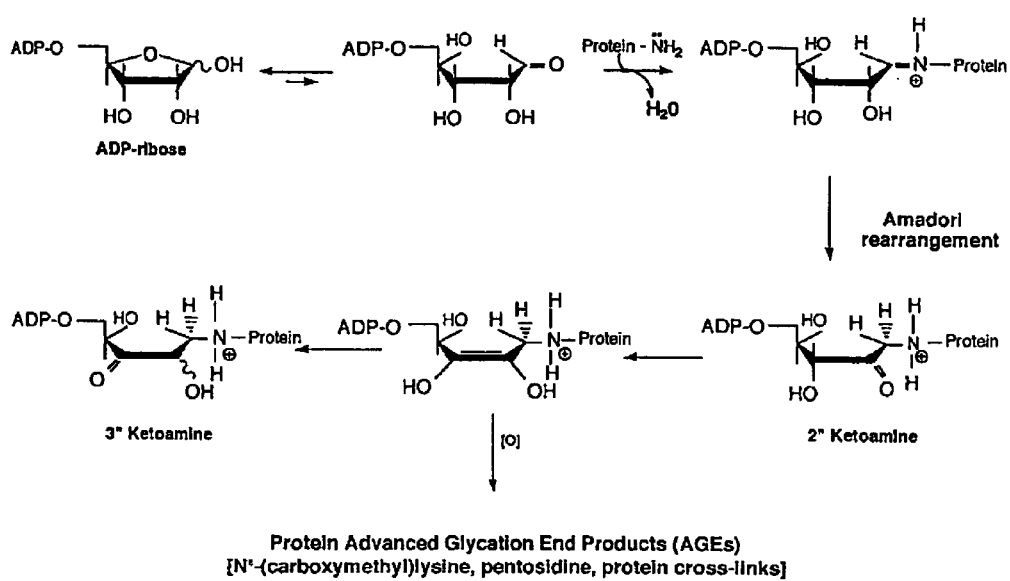
FIG. 3 presents the chemistry of glycation reactions via ADP-ribose.
Figure 4:
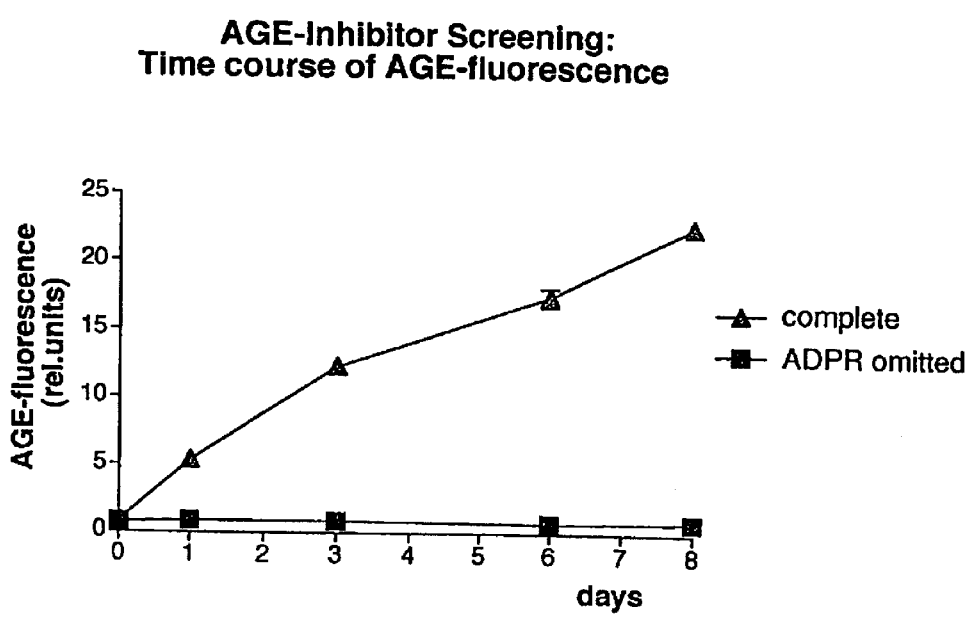
FIG. 4 sets forth data showing that the reaction between ADP-ribose and histone H1 proceeds rapidly at conditions resembling physiological conditions.
Figure 5:
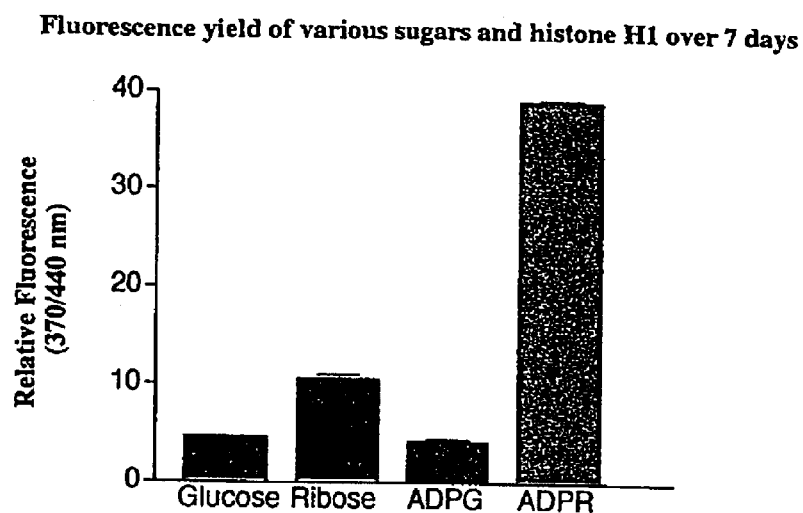
FIG. 5 compares glucose, ribose, ADP-glucose, and ADP-ribose in the method of the invention.
Figure 6:
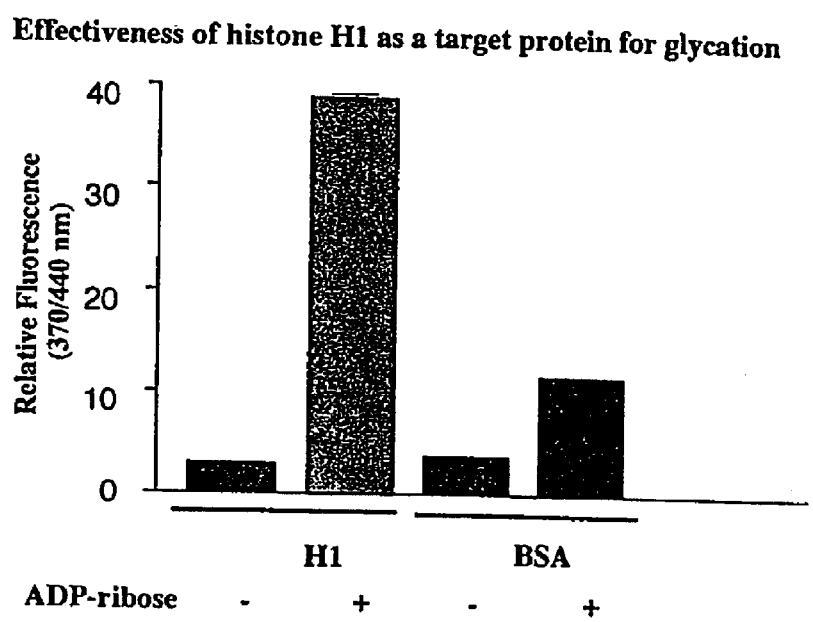
FIG. 6 compares bovine serum albumin and histone H1 as glycation targets.

It has been found that ADP-ribose and histone H1 undergo a fast, and potent glycation reaction, and this reaction is a key feature of the invention described herein. The chemistry of the glycation reactions by ADP-ribose is unique. These have been elucidated in detail, as shown in FIG. 3. Further, the reaction proceeds rapidly enough at conditions that simulate physiological conditions (50 mM phosphate buffer, pH7.4, as shown in FIG. 4), to warrant consideration of the assay as one useful in screening for compounds of interest, as described infra. Ketoamines and other, similar AGE products are formed by both ADP-ribose and glucose; however, the rate of formation of product by ADP-ribose is at least a thousand fold faster than formation by glucose (Cervantes-Laurean, et al., J. Biol. Chem. 271:10461–10469 (1996)). The reactions involving ADP-ribose are very fast; however, and this is key to the invention, the reaction pathways which involve ADP-ribose and histone H1 are similar, but much faster to those initiated by other sugars, suggesting that inhibitors of the rapid reaction between ADP-ribose and histone H1 should inhibit glycation reactions generally. For example, in a set of experiments which compared reaction of glucose, ribose, ADP-glucose and ADP-ribose with histone H1, the amount of fluorescent AGE generated from ADP-ribose far exceeded all others. See FIG. 5, depicting such assays, at the conditions set forth supra. Similarly, histone H1 is an excellent glycation target. FIG. 6 shows the results of experiments in which histone H1 was compared to bovine serum albumin as a glycation target. The potency of ADP-ribose as a glycating agent is known. The basic, lysine and arginine rich histone H1 is an excellent substrate. Hence, it has been observed that, under slightly alkaline conditions (i.e., about pH 9.0), the in vitro reaction between ADP-ribose and histone H1 proceeds within minutes, thereby generating AGE-fluorescence (Jacobson, et al., "ADP-Ribose In Glycation and Glycoxidation Reactions," in Koch-Nolte, ed., ADP-Ribosylation In Animal Tissues, Plenum Press, 1997, pages 371–379), and protein cross-linking.

Figure 7:
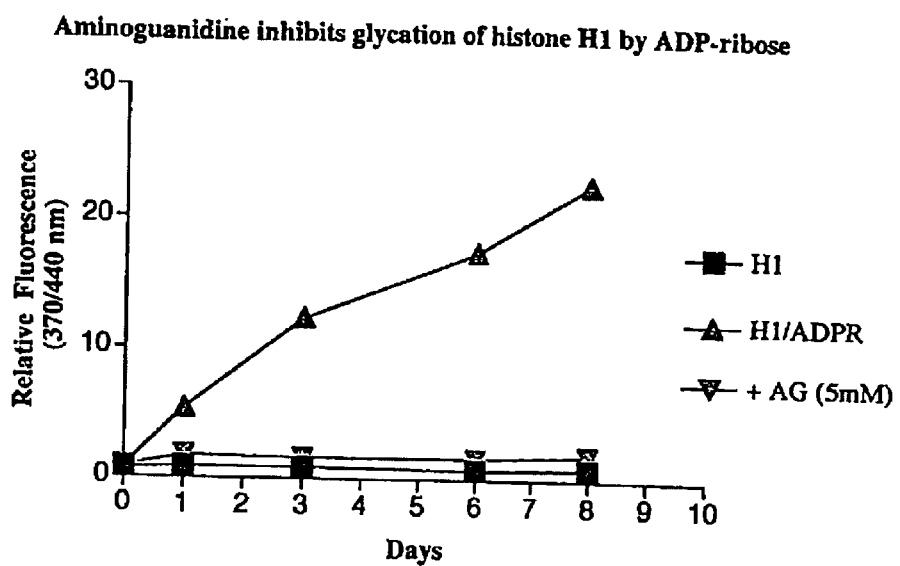
FIG. 7 shows that aminoguanidine suppresses the glycation of histone H1 by ADP-ribose.

For an assay to be effective in screening for compounds which either inhibit and/or enhance glycation, it should be tested with an agent with a known effect on the process under consideration. FIG. 7 presents data showing that, when the known glycation inhibitor aminoguanidine was tested, again at the physiological levels set forth supra, its inhibiting effect was detected very quickly. Hence, the assay described herein can be used as claimed.

Figure 8:
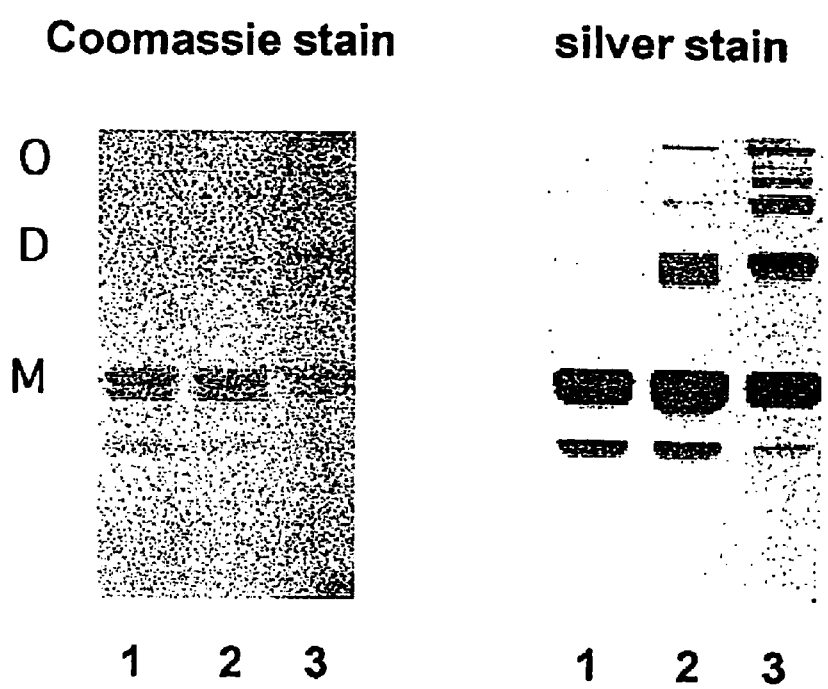
FIG. 8 measures formation of protein cross-linking in the histone H1/ADP-ribose reaction.
Figure 9:
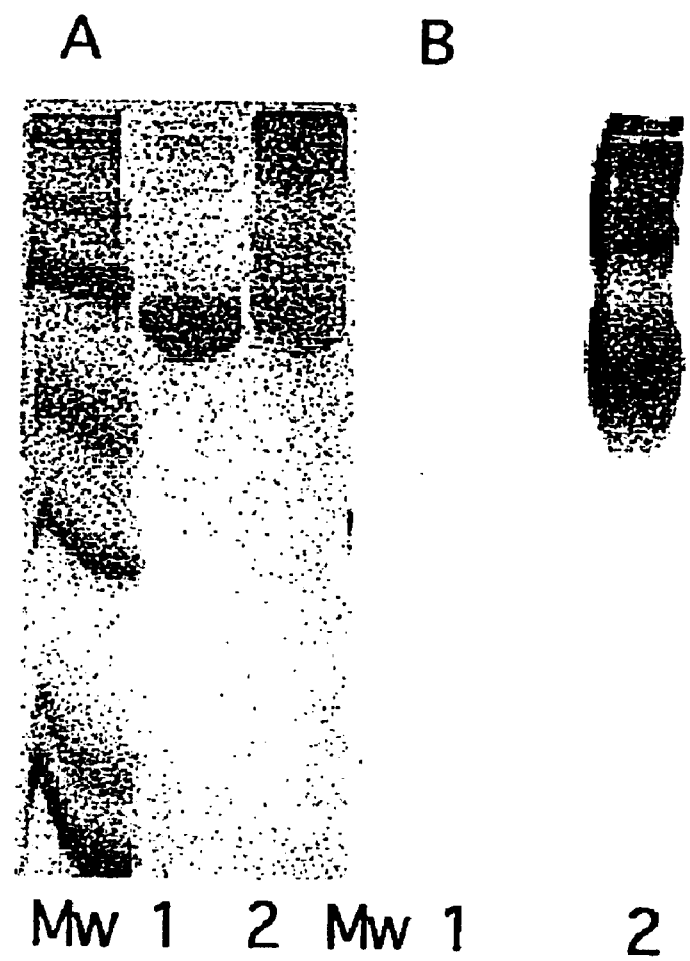
FIG. 9 presents results from experiments which measure protein carbonylation.

Additional data presented herein show that standard methods of measuring protein glycation indicated that AGE-type fluorescence that is measured does in fact measure protein damage. Both protein cross-linking and protein carbonylation are well established indicia of protein glycation. See Schacter, et al., Free Radic Biol Med. 17:429–437 (1994), incorporated by reference. In brief, following the assays described infra, formation of protein cross-linking was measured on 12% SDS-PAGE, followed by Coomassie and silver staining. These results are set forth in FIG. 8. Cross-linking was detectable with a high degree of sensitivity, when the reaction between ADP-ribose and histone H1 was carried out at pH 9.0. In FIG. 8, lane 1 shows time ("t" herafter)=0, while lanes 2 and 3 show t=2 and 24 hours, respectively. In FIG. 8, the abbreviations "M," "D", and "O" represent "monomer," "dimer" and "oligomer," respectively. Silver staining is the preferred way of determining the cross linking. Protein carbonlyation was determined via Western blotting. Specifically, AGE-BSA, which had been prepared by incubating BSA with 1.66M glucose, at pH 7.4 for 90 days at 37° C., was recognized after being derivatized with 2.4 dinitrophenlyhydrazine ("DNP"), when tested with antibodies specific for protein bound, DNP epitopes. This can be seen in lane 2, while lane 1 shows untreated BSA, which served as the control. In FIG. 9, panel A represents a Commasie stain, while panel B shows a carbonyl-immunostain.

In the examples which follow, the skilled artisan will appreciate that various embodiments and features of the invention are set forth.

EXAMPLE 1

Figure 10:
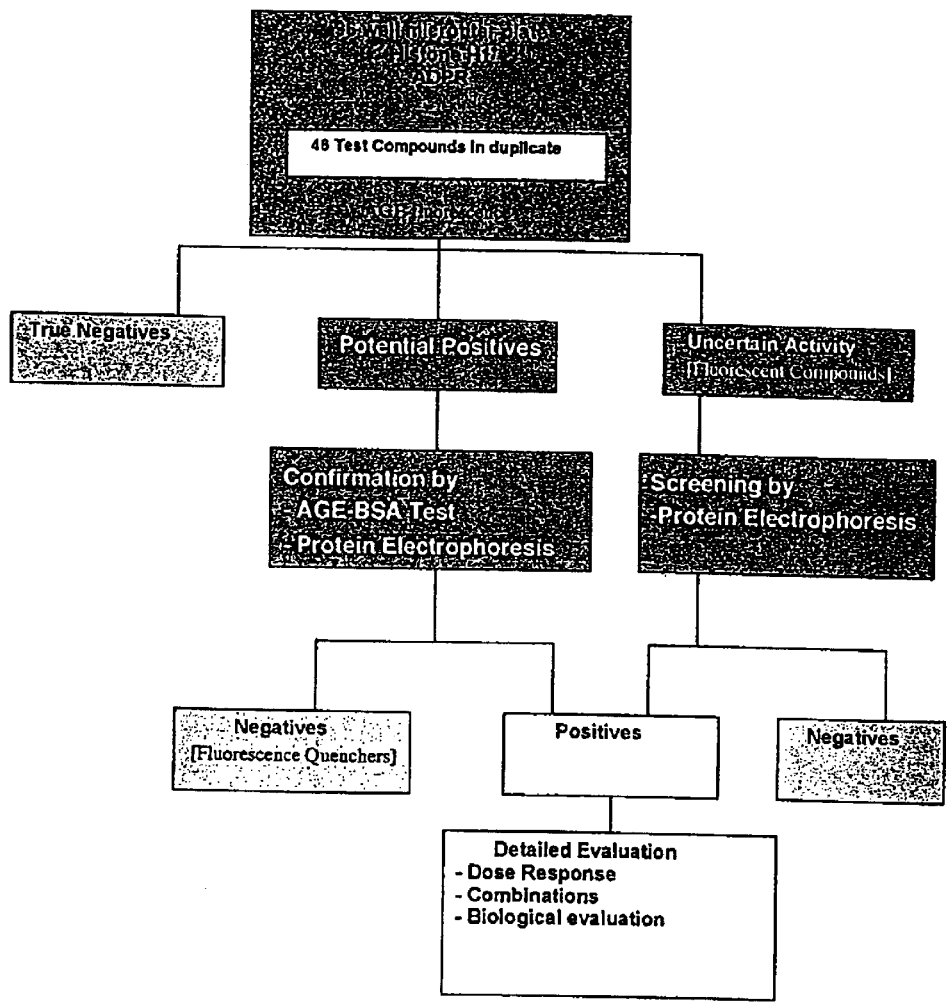
FIG. 10 elaborates a design for primary and secondary screening of inhibitors.

This example describes sets of experiments carried out in duplicate; however, it will be understood that such is not required, nor is it necessary to assay the number of samples assayed (48), in a 96-well, microtiter plate. It, and all other examples, are summarized in FIG. 10.

A 96-well, microtiter plate was used to carry out 48 reactions in duplicate. The first pair of wells contained the reactants ADP-ribose and histone H1, without any potential inhibitors. A second pair of wells contains the reactants and the known glycation inhibitor aminoguanidine, and functions as a positive control. Histone H1 is commercially available, and can be prepared following the procedures set out in Johns, et al., Biochem J. 92:55–59(1964), which is incorporated by reference herein.

Test compounds were added to the wells, at a level of 5 mM, or at the limit of solubility if this is below 5 mM. The reaction system is 50 mM potassium phosphate buffer, at pH 7.4 to which 1.5 mg/ml histone H1 and 1.0 mM ADP-ribose were added. Reaction volume was 300 ul. AGE-fluorescence was measured over time, with incubation at 37° C., at 355 nm (ex) and 405 nm (em). Upon comparison to the control, a test compound was deemed potentially positive if AGE-fluorescence was suppressed.

Figure 11:
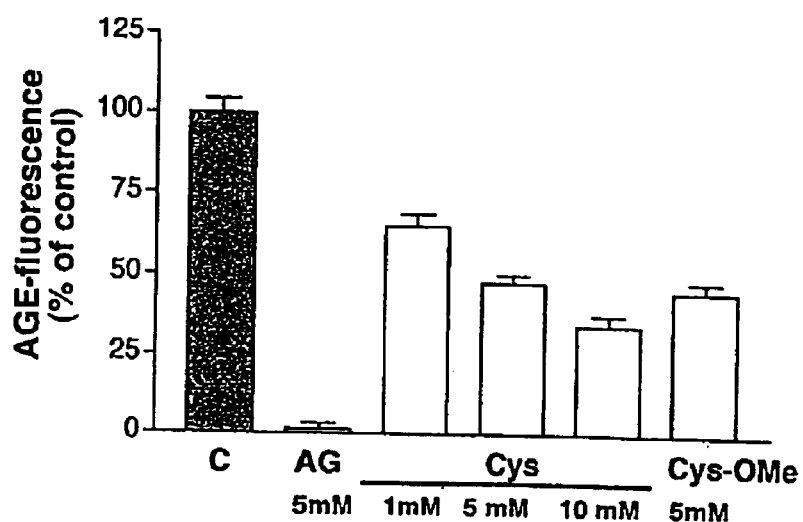
FIG. 11 presents data from experiments which identified potential inhibitors.
Figure 12:
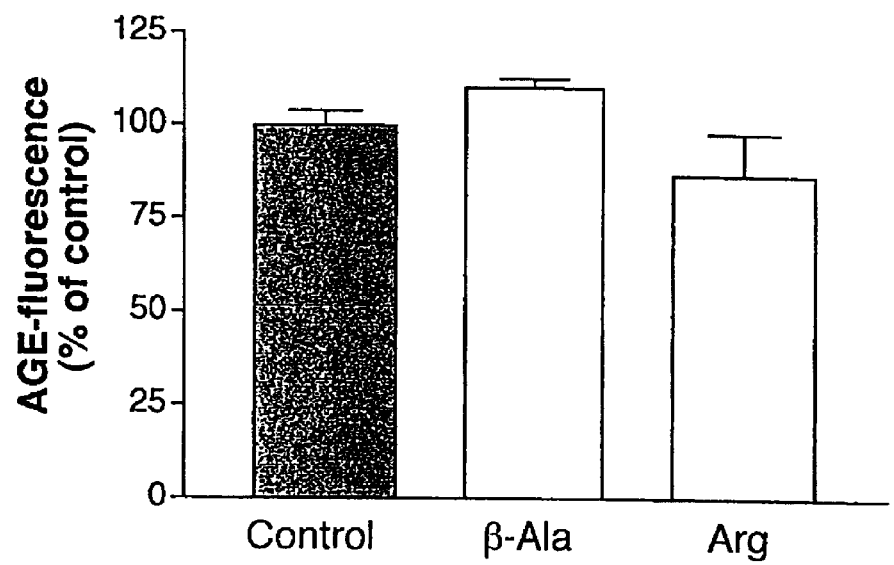
FIG. 12 presents data for two negative compounds, i.e., compounds which were not inhibitors of glycation.

FIG. 11 presents results from an assay which identified a potential inhibitor, i.e., cysteine and cysteine methylester. If a test compound did not suppress fluorescence, it was categorized as a true negative, and not pursued further. Both beta-alanine and arginine were found to be true negatives, as shown in FIG. 12.

False negatives can be determined easily, by measuring fluorescence at day 0, to determine autofluorescence. Any such compounds are tested in the secondary screen, described infra.

EXAMPLE 2

The foregoing example discussed true positives, true negatives, and false negatives. False positives are also possible, however. These suppress the formation of AGE-fluorescence by physical interference with fluorescence measurements. In order to eliminate such compounds, they are tested for their ability to quench AGE forms of bovine serum albumin ("AGE-BSA"), in the following assay.

AGE-BSA was prepared in accordance with Ikeda, et al., Biochemistry 35:8075–8083 (1996), incorporated by reference. The AGE-BSA was then added to a well which contained the test compound ADP-ribose and histone H1, and fluorescence was measured. The value obtained was compared to a value obtained when AGE-BSA was added to a well containing the inhibitor aminoguanidine. A decrease in AGE-BSA fluorescence in the presence of the potential compound results in classification as a negative, and exclusion from further screening. A general summary of the screening methodology that is elaborated in these examples, is set forth in FIG. 10.

EXAMPLE 3

This example describes a secondary screening, to further evaluate compounds which were deemed positive following the assays of examples 1 and 2. Specifically, it will be recalled that each sample was tested in two wells, one of which was tested in example 2, supra. The sample not used was analyzed, via 12% SDS-PAGE, followed by silver staining, in order to visualize protein cross-linking. This serves as an independent measure of glycation caused protein damage. A lack of protein damage indicates that the test compound actually does inhibit glycation.

Figure 13:
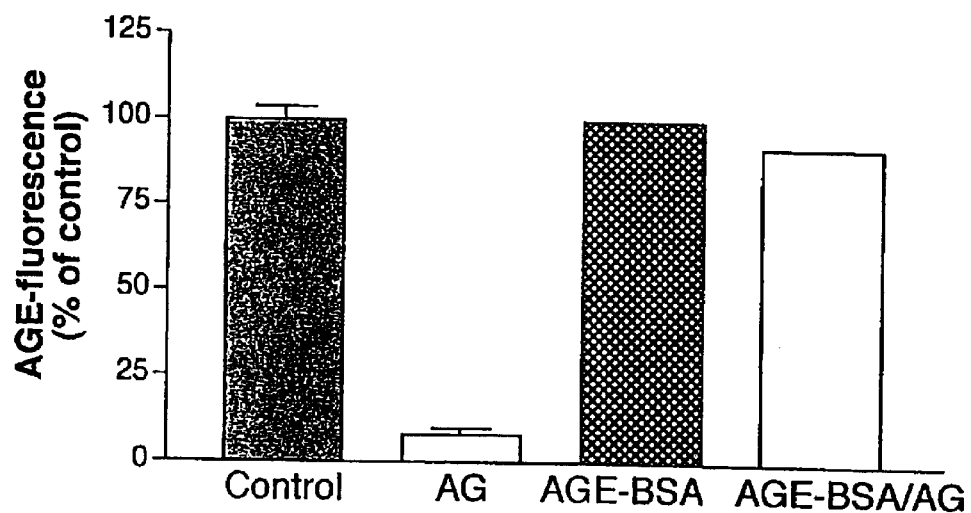
FIG. 13 depicts results from an assay designed to identify false positives.
Figure 14:
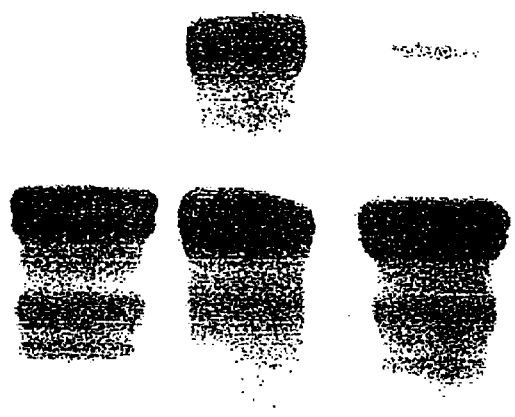
FIG. 14 shows results from a confirming cross-linking test to determine glycation, and hence protein damage.

Results of one such assay confirming a positive using fluorescence are shown in FIG. 13, and using the crosslinking test in FIG. 14.

EXAMPLE 4

These experiments describe the further development of the assay discussed supra.

To elaborate, histone H1 was isolated from fresh calfthymus. First, chromatin was extracted from samples of fresh calf thymus, via extraction with 0.14M NaCl and 0.05M $Na_2S_2O_5$, pH 5, in accordance with Wondrak, et al., Biochem J. 351: 769–777(2000), incorporated by reference. After repeated extraction with 5% $HClO_4$, and centrifugation at 1500×g, the histone H1 was precipitated from supernatant by adding TCA (20% final concentration v/v). Histone H1 precipitate was collected via centrifugation at 12,000×g, and deionized water. The sample was subjected to extensive dialysis (MW cut-off: 12,000–14,000) against water for 48 hours, and then lyophilized. SDS-PAGE (12%), was used to analyze sample purity. Any protein collected in this manner was stored at 4° C.

The histone H1 (1.5 mg/ml) was combined with 1 mM ADP-ribose, in 50 nM $KH_2PO_4$ buffer (pH 7.4, 37° C., 0.015% $NaN_3$ added, to inhibit microbial growth). This reaction mixture was added, to 96 well microtiter plates. Test compounds were added to the reaction mixture, at concentrations ranging from 1 to 10 mM, in reaction volumes of 300 ul. Texts were run in duplicate.

Accumulated protein damage was determined by measuring AGE-fluorescence, at wavelengths (λex=370 nm; λ em=440 nm. The fluorescence is suppressed in the presence of compounds with inhibitory activity. Assays were read on a conventional microtiter plate, with a filter setting that approached the above conditions (λ ex: 355 nm, λ ex: 405 nm), which is in the range of the broad excitation/emission maxima of AGE compounds.

The fluorescence was measured at the beginning, and after 5 days of incubation. Any compounds which are inherently fluorescent were identified by the initial measurement, and were considered false negatives; however, because they may in fact have inhibitory properties, they were tested in a second stage of the assay, described infra.

The known glycation inhibitor aminoguanidine was used as a control. In addition, histone H1 and ADP-ribose were assayed without a potential inhibitor, and histone H1 was also incubated without ADP-ribose.

After 5 days of incubation, the histone H1/ADP-ribose mixture produced AGE-fluorescence about 20 times greater than the background fluorescence produced by histone H1 alone. ADP-ribose incubated without histone H1 generated no fluorescence.

This first phase of the assay identified potential inhibitors; however, it was possible that such compounds were fluorescence quenchers rather than glycation inhibitors. As such, these were tested in an additional assay, as described infra.

To summarize, this step of the screening assay identified true negatives, which need not be considered further. It also identified compounds which might be inhibitors of glycation, and compounds with uncertain activity. These latter two classes of compounds were tested in assays now described.

EXAMPLE 5

These experiments describe how false positives, i.e., fluorescence quenchers, are identified and excluded from the potential positives identified in Example 1. Essentially, an AGE modified protein having known fluorescence activity was used, in a mixture of the test compound and other materials described above.

"AGE-BSA", or AGE modified bovine serum albumin has known fluorescence activity. It was prepared in accordance with Takata, et al., J. Biol. Chem. 263: 14819–14825 (1988), incorporated by reference. In brief, five days after development of fluorescence in the assay described supra 1.6 g of bovine serum albumin ("BSA") and 3.0 g of D-glucose were dissolved in 10 ml of 0.5M sodium phosphate buffer, pH 7.4, containing 0.05% $NaN_3$. The solution was filter sterilized through a 0.45 um filter, and incubated in the dark for 90 days at 37° C. The samples were dialyzed against water, and then lyophilized.

The tests were run by adding 1 mg/ml of the AGE/BSA to the reaction mixtures, as described supra. Any compounds which quench the inherent fluorescence of the AGE-BSA molecule were deemed false positives, and were excluded from further analysis.

EXAMPLE 6

The next step of the screening methodology involved assaying potential inhibitors to determine their ability to inhibit protein cross linking. To test this, reaction aliquots of the 5 day incubation mixtures, described in Example 1, supra, were assessed on 12% SDS-PAGE. Both untreated histone H1, and the aminoguanidine containing positive control were tested in the same way. All were visualized by silver staining.

The results of the experiments described in Examples 1–5 are set forth in the Table which follow. The fluorescence measurement of NADH on day 0 showed it to be a strongly fluorescent substance, i.e. a compound with unknown activity. When it was tested in cross linking experiments, however, it showed no inhibitory activity. Hence, the combination of assays show that the compound is a "true" negative. Rutin was identified as a false positive, because it quenched AGE-BSA fluorescence, but did not inhibit histone H1 cross linking.

TABLE 1

Screening of inhibitors of nonoxidative advanced glycation: AGE-fluorescence on 96 well-microtiter plates

| sample | AGE-fluorescence (day 0) | AGE-fluorescence (day 5) | % inhibition | AGE-BSA test |
|---|---|---|---|---|
| histone H1 blank complete reaction | 1.1 (0.) | 1.5 (0.2) | | |
| under argon (+5 mM DPTA) | 1.1 (0.1) | 23 (1.1) | | 32 |
| under air + compound | 1.1 (0.1) | 21 (0.9) | | 30 |
| Aminoguanidine | | | | |
| 1 mM | 1.2 (0.1) | 4.3 (0.2) | 84 | |
| 5 mM | 1.2 (0.1) | 2.2 (0.0) | 96 | |
| 10 mM | 1.3 (0.1) | 1.8 (0.0) | 97 | 10 |
| Rutin 200 μM | 1.1 (0.0) | 3.0 (0.1) | 90 | 5.7 |
| NADH 5 mM | 52 (0.3) | 31 (0.0) | | |
| L-Cys-Gly | | | | |
| 1 mM | 1.3 (0.3) | 17 (0.0 | 20 | |
| 5 mM | 1.2 (0.2) | 26 (0.4) | 0 | |
| 10 mM | 1.2 (0.1) | 40 (0.0) | 0 | |
| GSH | | | | |
| 1 mM | 1.3 (0.0) | 19 (0.3) | 10 | |
| 5 mM | 1.1 (0.3) | 17 (0.3) | 20 | |
| 10 mM | 1.1 (0.0) | 14 (0.5) | 35 | |
| L-Cys | | | | |
| 1 mM | 1.2 (0.1) | 14 (0.3) | 36 | |
| 5 mM | 1.1 (0.1) | 11 (0.2) | 50 | |
| 10 mM | 1.2 (0.1) | 9.0 (0.2) | 61 | |
| L-Cys-OMe | | | | |
| 1 mM | 1.2 (0.1) | 15 (0.1) | 31 | |
| 5 mM | 1.3 (0.1) | 12 (0.8) | 46 | |
| 10 mM | 1.2 (0.1) | 9.0 (0.2) | 61 | |
| NAC | | | | |
| 1 mM | 1.2 (0.2) | 11 (0.6) | 51 | |
| 5 mM | 1.0 (0.1) | 10 (0.4) | 55 | |
| 10 mM | 1.1 (0.1) | 9.4 (0.6) | 58 | |
| D,L-Homocysteine | | | | |
| 1 mM | 1.3 (0.0) | 16 (1.1) | 26 | |
| 5 mM | 1.2 (0.2) | 22 (0.1) | 0 | |
| 10 mM | 1.1 (0.1) | 27 (1.7) | 0 | |
| Cysteamine | | | | |
| 1 mM | 1.0 (0.1) | 10 (0.6) | 55 | |
| 5 mM | 1.1 (0.1) | 9.0 (0.7) | 60 | |
| 10 mM | 1.2 (0.2) | 6.0 (0.3) | 76 | |
| D,L-Penicillamine | | | | |
| 1 mM | 1.1 (0.2) | 13 (0.0) | 40 | |
| 5 mM | 1.1 (0.1) | 2.7 (0.0) | 92 | |
| 10 mM | 1.1 (0.1) | 1.7 (0.0) | 97 | 15 |
| D-Penicillamine | | | | |
| 1 mM | 1.2 (0.0) | 11 (0.6) | 51 | |
| 5 mM | 1.1 (0.1) | 2.9 (0.3) | 91 | |
| 10 mM | 1.1 (0.0) | 1.4 (0.1) | 99 | 12 |

TABLE 1-continued

Screening of inhibitors of nonoxidative advanced glycation:
AGE-fluorescence on 96 well-microtiter plates

| sample | AGE-fluorescence (day 0) | AGE-fluorescence (day 5) | % inhibition | AGE-BSA test |
|---|---|---|---|---|
| 2-Thiobarbituric acid | | | | |
| 1 mM | 1.1 (0.1) | 12 (0.4) | 45 | |
| 5 mM | 1.2 (0.1) | 5.5 (0.4) | 78 | |
| 10 mM | 1.3 (0.1) | 2.3 (0.0) | 95 | 12 |
| L-Ergothioneine | | | | |
| 1 mM | 1.0 (0.1) | 13 (0.0) | 40 | |
| 5 mM | 1.2 (0.0) | 9.3 (0.2) | 59 | |
| 10 mM | 1.2 (0.1) | 7.4 (0.1) | 69 | |
| Thiourea | | | | |
| 1 mM | 1.1 (0.1) | 18 (0.1) | 15 | |
| 5 mM | 1.1 (0.1) | 15 (0.0) | 30 | |
| 10 mM | 1.1 (0.2) | 11 (0.3) | 50 | |

EXAMPLE 7

Figure 15:
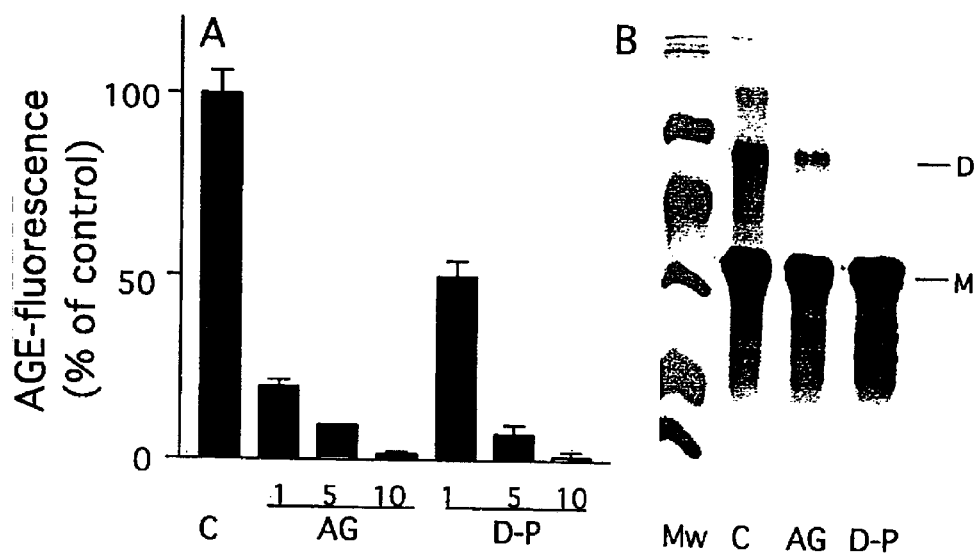
FIG. 15 shows the results of experiments which showed the ability of various compounds to inhibit glycation induced cross-linking of histone H1.

Nucleophilic compounds have the potential to scavenge electrophilic, α-dicarbonyl intermediate compounds. See, e.g., Ferguson, et al., Chem. Res. Tox 12: 617–622 (1999). As such, these compounds should show promise as inhibitors of advanced glycation. Several of the thiol compounds tested showed inhibitory activity, including L-cysteine methylester ("L-cys-OMe,") L-cysteine (L-Cys), and N α-acetyl-L-cysteine (NAC); however, they only showed 61% inhibition at the highest concentration tested, 10 mM. The thiol cysteamine and the mercaptomidazole derivative L-ergothioneine showed somewhat better inhibition, while D, L-homocysteine, and $NH_2$-L-cys-gly-COOH increased AGE-fluorescence, indicating that these probably undergo gylcation reactions themselves. D-penicillamine and the racemic mixture D, L-penicillamine were the best of the compounds tested. The compounds, when tested with AGE-BSA, were found not to be false positives. Hence, their inhibitory potential was tested, i.e., their ability to inhibit glycation induced cross linking of histone H1. Indeed, their inhibitory effects were found to be more potent than aminoguanidine. The results are set forth in FIG. 15, which shows both fluorescence as compared to fluorescence with aminoguanidine, and the results of analysis of cross-linking. These data show that 1-amino-2-mercapto-2,2-dimethylethane is the phamacaphor, i.e., the active portion of the molecule involved in inhibiting AGE-protein formation.

EXAMPLE 8

The inhibitory activity exhibited by D-penicillamine suggested that it acted as a scavenging agent toward reactive carbonyl species. To test this, experiments were carried out to assess chemical reactivity toward α-dicarbonyl compounds, at physiological pH and temperature.

A solution of D-penicillamine (350 mg, 2.3 mmol) was prepared in 50 ml of aqueous 0.2M phosphate buffer (pH 7.4) and methylglyoxal (40% in $H_2O$/620 ul, 3.45 mmol) was added to it. The mixture was stirred for 24 hours at 37° C., after which the solvent was concentrated to half volume at reduced pressure, followed by desalting on a column. The column was developed with water, UV absorbing peaks were pooled, and water was evaporated at reduced pressure. Crude product was purified via anion exchange chromatography on a 1.5×45 cm QAE Sephadex column, which was developed by application of a linear gradient formed between 200 ml of distilled water, and 200 ml of 0.2M $NH_4HCO_3$. Fractions were collected and absorbance at 254 nm was measured.

Figure 16:
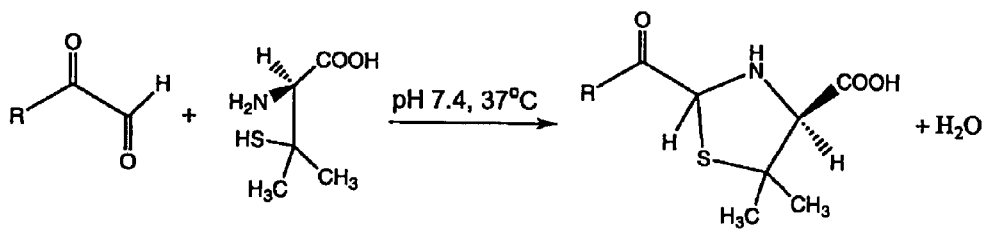
FIG. 16 shows the structures of various reactants that were identified in an $^1$H-NMR spectral analysis.

The $^1$H-NMR spectrum exhibited the following signals: [δ $_H$($D_2O$) in ppm]: 1.03 (3H, s, $CH_3$); 1.05 (3H, s, $CH_3$); 1.90 (3H, s, CO—$CH_3$); 3.96 and 3.98 (diastereoisomeric, 1H, s, Ch—COOH). Mass spectrometric analysis via "MALD-TOF-MS" revealed a [M+Na]$^+$ of226 Da. This is comparable with calculated mass for $C_8H_{13}NO_3S$, which is 203.26 Da. The aldehyde-thiazolidine adduct formed, presumably, after nucleophilic ring closure of the initially formed, Schiff base. See FIG. 16 for structures of the reactants.

All $^1$H-NMR signals could be assigned to 2-acetyl-5,5-dimethyl-thiazolidine-4-carboxylic acid as the structure of the reaction product. The only exception is the missing signal of the very acidic protein in position 2 of the thiazolidine ring, which probably exchanges with $D_2O$. No aldehyde proton was detected, excluding formation of the isomeric thiazolidine at C-2 of methylglyoxal. Further, C-NMR analysis of the compound clearly indicated two carbonyl groups, at δ=199 ppm ($CH_3C$=O), and δ=209 ppm (COOH).

To learn more about the reaction, D-penicillamine was reacted with phenylglyoxal. In the fashion described supra, phenylglyoxal, at final concentration of 10 mM, and D-penicillamine, at final concentration of 20 mM were reacted in 50 mM $KH_2PO_4$ buffer, pH 7.4, at room temperature. Reaction progress was monitored via HPLC analysis of reaction aliquots at 254 nm. After 40 minutes, more than 90% conversion of phenylgloxal peak into a single peak was observed. The product was obtained via preparative HPLC, was lyophilized, and analyzed by H-NMR spectroscopy.

The spectrum exhibited the following signals: [δ H ($D_2O$) in ppm]: 1.38 (3H$_S$, $CH_3$), 1.45 (3H, s, $CH_3$), 4.12 (1H, s, CH—COOH), 7.42–7.82 (5H, m, ArH). Again, a signal corresponding to the acidic proton in position 2 of the thiazolidine ring was not detected, due to the expected exchange with $D_2O$, and no aldehyde proton was observed. Thus, the structure of the phenylglyoxal-D-penicillamine adduct was assigned as 2-benzoyl-5,5-dimethyl-thiazolidine-4-carboxylic acid.

The observed structures suggest that α-dicarbonyl trapping by 2-acyl-5,5-dialkyl-thiazolidine formation as a mechanism of inhibition of nonoxidative advanced gylcation may explain the efficacy of inhibition of D-penicillamine. The 5,5-dialkyl substitution may sterically favor closure of the thiazolidine ring, preventing the reverse reaction by hydrolysis.

EXAMPLE 9

The experiments described in this example were designed to evaluate the relative rates of α-dicarbonyl trapping by D-penicillamine and animoguanidine, using phenylglyoxal as a model.

Reactions were carried out in 10 mM phosphate buffer, pH 7.4, at 37° C., and were followed by HPLC analysis. Phenylglyoxal was used at a concentration of 50 mM, while D-penicillamine and aminoguanidine were used at concentrations of 250 mM, and 500 mM. The phenylglyoxal was used as a UV active, α-oxoaldehyde compound. Over the course of the reaction, aliquots were analyzed via HPLC.

For reactions involving D-penicillamine, aliquots were taken at 20 second intervals and kept on dry ice for analysis. Initial reaction rates of phenylglyoxal and test compounds were monitored by following the disappearance of phenylglyoxal over time.

The reaction between phenylglyoxal and test compounds is a second order reaction, where the rate equation is:

$$\frac{-dc}{dt} = (k_{2nd})[\text{phenylglyoxal}][\text{dicarbonyl scavenger}]$$

As can be seen from the concentration of reactants, there was excess test compound in all reactions (1:5, or 1:10), in order to convert the reaction to pseudo—first order reaction kinetics, since the reaction rate constant ($k_{1st}$) apparently depends on concentration of the test compound.

A plot of log AUC for phenylglyoxal versus time resulted in a slope of $k_{1st}/2.303$. The measured, first order rate constant ($k_{1st}$) was used to calculate the second order rate constant ($k_{2nd}$), according to:

$$k_{2nd} = k_{1st}[\alpha\text{-dicarbonyl scavenger}]$$

The calculated second order rate constants were determined at two reactant rates (5:1, and 10:1), and were in good agreement.

D-penicillamine trapped phenylglyoxal more than 60 times faster than aminoguanidine. In order to determine if the α-oxo substitution had any impact on the progress of the aldehyde trapping reaction, the reactivity of D-penicillamine with the aldehyde corresponding to phenylglyoxal, i.e., phenylacetaldehyde, was carried out, in the same manner as is described herein.

D-penicillamine was found to trap phenylacetaldehyde about 14 times less efficiently than phenylglyoxal, leading to the conclusion that D-penicillamine traps α-oxo carbonyl compounds more efficiently than aldehydes.

EXAMPLE 10

Compounds such as glyoxal and methylglyoxal have been established as being toxic to cells, such as neuronal cells (Kikuchi, et al., J. Neurosci Res. 57: 280–289 (1999); Shinpo, et al., Brain Res. 861: 151–159(2000), and macrophage derived cell lines (Okada, et al., Biochem. Biophys. Res. Commun. 225:219–229 (1996). As such, the ability of α-dicarbonyl scavengers to protect against α-dicarbonyl toxicity was tested.

Continuously cultured cell lines "He-Cat" (human epidermal keratinocytes), and "CF-3" (human dermal fibroblasts), were cultured under standard conditions, divided biweekly into DMEM containing 10% fetal bovine serum, and were kept in a humidified atmosphere containing 5% $CO_2$ at 37° C. In order to divide the cells, 5% trypsin was used on the keratinocytes, and 1% trypsin was used on the fibroblasts.

Keratinocytes were seeded at $2 \times 10^4$ cells/well, and fibroblasts at $4 \times 10^4$ cells/well, using 6 well dishes. The cells were allowed to attach to the plate overnight. Either D-penicillamine or aminoguanidine (1 mM each) was added to the plates 15 minutes prior to addition of glyoxal or methylglyoxal. The α-dicarbonyl was left for 72 hours. Varying concentrations of the α-dicarbonyl were used. Cells were counted with a Coulter counter after 72 hours of stress. Cultures were also run where the glyoxal or methylglyoxal was used without the scavenger. L-alanine was used as a negative control as it was not expected to have protective effect.

Figure 17:
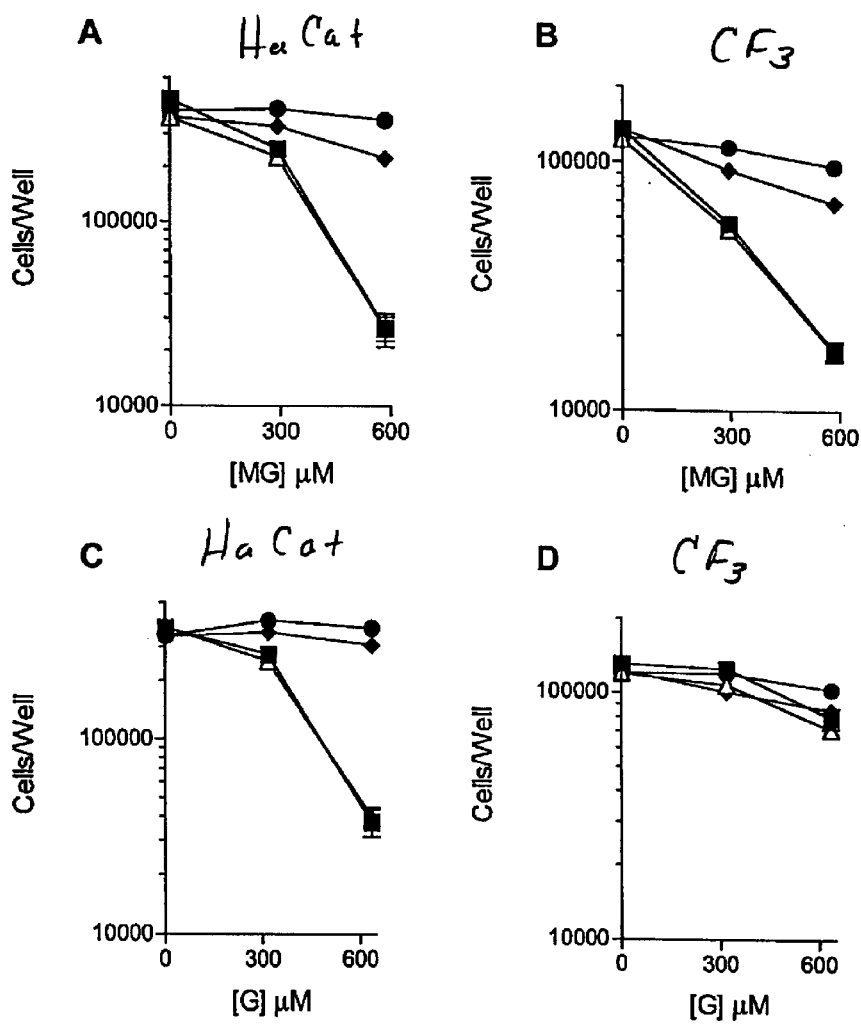
FIGS. 17 and 18 depict results of experiments designed to determine the protective effect of D-penicillamine on cells.

The results indicated that increasing concentrations of methylglyoxal resulted in dose dependent growth inhibition with concentrations of 600 μM completely inhibitory to both lines. Glyoxal effected both cell types equally, while fibroblasts were less sensitive toward glyoxal. L-alanine showed no protective effect. Aminoguanidine rescued both cell lines from methylglyoxal induced growth inhibition in part, while D-penicillamine were superior, and almost completely blocked methylglyoxal's toxicity. Both compounds appeared to protect keratinocytes against growth inhibition by glyoxal. The protective effect can be seen in FIG. 17. Presumably, direct scavenging of toxic, reactive carbonyl agents are the cause, because preincubation of cells with the protective compounds for 24 hours followed by exposure to the α-dicarbonyls did not show any protective effect.

Figure 18:
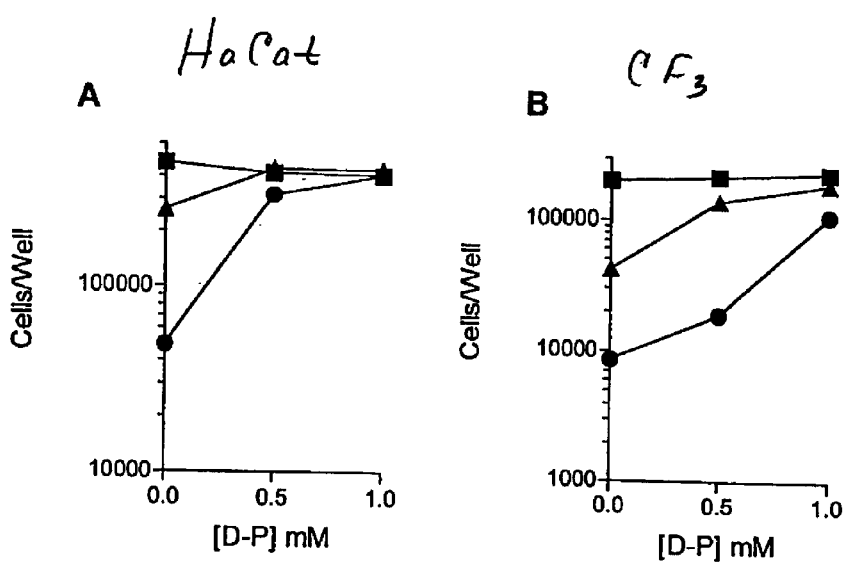

It was of interest to determine if D-penicillamine exhibited a dose range, cyto-protective effect. Increased concentration of D-penicillamine resulted in increased protection. It was observed that fibroblasts were, in fact, more sensitive to methylglyoxal activity than keratinocytes, with D-penicillamine showing 47% survival in fibroblasts treated with 600 4M methylglyoxal, as compared to 100% survival of keratinocytes. FIG. 18 shows this.

EXAMPLE 11

This example is also reported in Wondrak, et al., Biochem J. 351:769–777 (2000), incorporated by reference.

The examples described herein show the potency of ADP-ribose in causing histone H1 carbonylation. It is also reported, supra, that glucose reacts weakly.

A series of experiments were carried out to compare different reducing sugars as glycation agents. In addition to ADP-ribose, ADP-glucose, D-ribose and D-glucose were tested. Briefly, histone H1 was combined with 1 mM of each sugar, and the mixture was incubated at pH 7.4. After 7 days of incubation, reaction aliquots were analyzed on 12% SDS-PACE gels, with silver staining. Results are presented in FIGS. 19A and B. In each of these, lane 1 is a control, with no sugar added, while lanes 2–5 show results using D-glucose, D-ribose, ADP-glucose, and ADP-ribose, respectively. ADP-ribose caused extensive carbonylation, while D-ribose caused a lesser amount. Neither D-glucose nor ADP-glucose caused significant carbonylation. The amount of carbonylation caused by ADP-ribose (0.82 mole/mole histone H1), and D-ribose (0.06 mole/mole histone H1) correlated with immunostaining.

Figure 19:
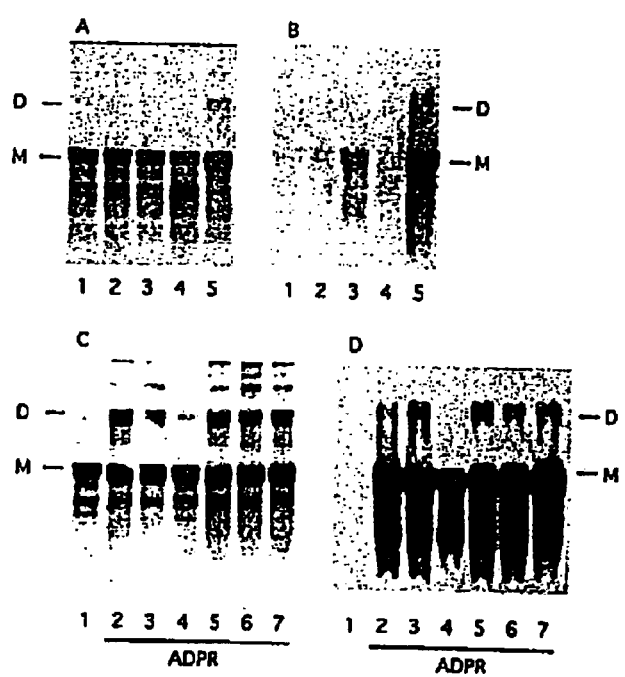
FIGS. 19A–D show studies on the effect of various sugars (A and B), and inhibitors (C and D).

In order to determine if the carbonylation of histone H1 by ADP-ribose involved an oxidative pathway, several compounds, known to interfere with glycoxidation of proteins by D-glucose were tested to determine if they interfered with this action by ADP-ribose. The compounds tested included 5 mM DTPA under argon, 5 mM aminoguanidine, 5 mM $N^\alpha$ acetyl L-cysteine, 5 mM mannitol, and 100 units/ml catalase. These results are depicted in FIGS. 19C and D, and show that none of these interfered with the carbonylation, with the exception of aminoguanidine, which showed a slight effect. Protein cross linking, however, was fully blocked, suggests that the carbonylation of histone H1 by ADP-ribose is a result of early glycation, rather than glycoxidation.

The foregoing disclosure sets forth various aspects of the invention, which relates to a method for identifying substances which effect cellular stress. "Cellular stress" as used herein refers to stress induced by, e.g., oxidative stress, glycation, UV radiation, and so forth. This, in turn, leads to tissue deterioration and aging. Preferably, the method relates to identifying substances which act as carbonyl scavengers, such as dicarbonyl scavengers, and thus inhibit formation of protein-AGE products. In parallel, these assays permit the artisan to eliminate antioxidants in the screening assay, because the assays function in the absence of oxygen. Hence, one can identify dicarbonyl scavengers using this method, and can also screen compounds to determine whether or not they function as antioxidants.

As indicated, supra, the method essentially involves admixing a compound or substance under study with the protein histone H1 and ADP-ribose. Histone H1 and ADP-ribose are known to interact, leading to formation of a fluorescent product. If the compound of interest, when admixed with the histone H1 and ADP-ribose results in a reduction of fluorescence, the substance may be an inhibitor of protein-AGE formation. Conversely, agonists of protein-AGE formation may be identified in the same way.

As the examples indicate, substance of interest may be tested in at least two different additional assays, including one where the substance is admixed with AGE-BSA as well as histone H1 and ADP-ribose, and an assay to determine if molecules of histone H1 have cross linked, when these were combined with ADP-ribose and the substance of interest.

Of particular interest are compounds considered to be nucleophilic, thiol containing compounds in particular. As the examples show, compounds with the desired properties were identified in this way.

It is noted that one can measure glycation of compounds in many ways. For example, the art is familiar with assays for determining fructosamine content of molecules, and such are, in fact, assays for determining glycation. These, as well as other assays, can be used in this invention.

In preferred embodiments, at least two different assays are carried out, so as to confirm the results developed in a first assay, but such is not required. Further, the assays can be run, in tandem, with either a positive control, a negative control, or most preferably with both. Again, the type of control assay used may vary, and this is at the discretion of the skilled artisan.

In addition to the assays of the invention, kits are also a part thereof. These kits comprise, at minimum, a container means, such as a box, which then contains separate portions of each of ADP-ribose and histone H1, in solution, lypholized, powdered, tablet or some other form convenient to the artisan. Such kits preferably contain instructions for carrying out the assay, and may optionally contain samples of one or both of a positive and negative control reagent, such as those described supra.

Other aspects of the invention will be clear to the skilled artisan, and need not be elaborated further.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

We claim:

1. A method for determining if a substance is an inhibitor of protein glycation, comprising:

(i) admixing ADP-ribose and histone H1 and determining fluorescence, (ii) admixing ADP-ribose, histone H1, and said substance, and determining fluorescence, (iii) comparing measured fluorescence in (i) and (ii), wherein a decrease in measured fluorescence in (ii) as compared to (i) is indicative of a possible protein glycation inhibitor, (iv) combining said possible protein glycation inhibitor with AGE-BSA, and measuring fluorescence, (v) measuring fluorescence of an amount of AGE-BSA equal to that in (iv), (vi) comparing fluorescence in (iv) and (v), wherein a decrease of fluorescence in (iv) as compared to (v) is indicative of a false positive, which quenches AGE fluorescence, and (viii) combining said substance if it does not quench AGE fluorescence with a protein, and determining damage done to said protein by said substance, wherein a lack of said damage indicates said substance is an inhibitor of protein glycation.

2. The method of claim 1, wherein said substance is a dicarbonyl scavenger.

3. The method of claim 1, wherein said substance is not an antioxidant.

4. The method of claim 1, comprising measuring fluorescence in steps (i) and (ii) about 5 days after admixing.

5. The method of claim 1, further comprising determining damage done to said protein by said substance by determining cross-linking of molecules of histone H1.

6. The method of claim 1, wherein said substance is a nucleophilic compound.

7. The method of claim 6, wherein said nucleophilic compound is a thiol containing compound.

* * * * *